United States Patent
Baran et al.

(10) Patent No.: US 9,790,977 B2
(45) Date of Patent: Oct. 17, 2017

(54) PEN-TYPE INJECTION DEVICE AND ELECTRONIC CLIP-ON MODULE THEREFOR

(71) Applicant: Sanofi-Aventis Deutschland GmbH, Frankfurt am Main (DE)

(72) Inventors: Andre Baran, Steinfurt (DE); Kay Behrendt, Bad Bentheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/375,113

(22) PCT Filed: Feb. 8, 2013

(86) PCT No.: PCT/EP2013/052507
§ 371 (c)(1),
(2) Date: Jul. 28, 2014

(87) PCT Pub. No.: WO2013/120775
PCT Pub. Date: Aug. 22, 2013

(65) Prior Publication Data
US 2015/0018770 A1   Jan. 15, 2015

Related U.S. Application Data

(60) Provisional application No. 61/604,702, filed on Feb. 29, 2012.

(30) Foreign Application Priority Data

Feb. 13, 2012   (EP) .................................. 12155199

(51) Int. Cl.
*A61M 5/24* (2006.01)
*F16B 21/08* (2006.01)
(Continued)

(52) U.S. Cl.
CPC ............ *F16B 21/088* (2013.01); *A61M 5/24* (2013.01); *A61B 5/14532* (2013.01);
(Continued)

(58) Field of Classification Search
CPC .... A61M 2205/582; A61M 2205/6045; A61M 5/24; Y10T 29/49826; Y10T 403/59; F16B 21/088
See application file for complete search history.

(56) References Cited

U.S. PATENT DOCUMENTS 6,482,185 B1   11/2002   Hartmann
7,740,612 B2   6/2010   Hochman
(Continued)

FOREIGN PATENT DOCUMENTS

CN   101454037 A   6/2009
CN   101534883 A   9/2009
(Continued)

OTHER PUBLICATIONS

English Translation of Abstract of the Japanese Patent Application No. 2005-287676 dated May 24, 2017.
(Continued)

*Primary Examiner* — Kevin C Sirmons
*Assistant Examiner* — Deanna K Hall
(74) *Attorney, Agent, or Firm* — McDonnell Boehen Hulbert & Berghoff LLP

(57) ABSTRACT

The present invention relates to a supplementary device for a manually operable injection device. The device has a body and a mating unit configured to releasably mount the body to the injection device in a specific position relative to an outside surface of the injection device.

20 Claims, 12 Drawing Sheets

(51) Int. Cl.
  *A61B 5/145*  (2006.01)
  *A61M 5/31*   (2006.01)
  *G06F 19/00*  (2011.01)
  *A61B 5/00*   (2006.01)

(52) U.S. Cl.
  CPC .... *A61B 5/4839* (2013.01); *A61M 2005/3125* (2013.01); *A61M 2005/3126* (2013.01); *A61M 2205/14* (2013.01); *A61M 2205/18* (2013.01); *A61M 2205/3306* (2013.01); *A61M 2205/3375* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/6045* (2013.01); *A61M 2205/6072* (2013.01); *A61M 2205/6081* (2013.01); *A61M 2209/04* (2013.01); *G06F 19/3468* (2013.01); *Y10T 29/49826* (2015.01); *Y10T 403/59* (2015.01)

(56) References Cited

U.S. PATENT DOCUMENTS

| | | | |
|---|---|---|---|
| 9,064,107 B2 | 6/2015 | Reggiardo et al. | |
| 9,072,833 B2 | 7/2015 | Jennings et al. | |
| 9,089,650 B2 | 7/2015 | Nielsen et al. | |
| 2010/0286612 A1* | 11/2010 | Cirillo | A61M 5/31525 604/111 |
| 2011/0313349 A1* | 12/2011 | Krulevitch | A61M 5/24 604/65 |

FOREIGN PATENT DOCUMENTS

| | | |
|---|---|---|
| CN | 101848742 A | 9/2010 |
| CN | 102170929 A | 8/2011 |
| EP | 2060284 A1 | 5/2009 |
| EP | 2182456 A1 | 5/2010 |
| JP | 2001299936 A | 10/2001 |
| JP | 2005287676 | 10/2005 |
| WO | 2007107564 A1 | 9/2007 |
| WO | 2009024562 A1 | 2/2009 |
| WO | 2010037828 A1 | 4/2010 |
| WO | 2010098927 A1 | 9/2010 |
| WO | 2010128493 A2 | 11/2010 |
| WO | 2011117212 A1 | 9/2011 |

OTHER PUBLICATIONS

English Translation of Abstract of the Japanese Patent Application No. 2001-299936 dated May 24, 2017.

* cited by examiner

PEN-TYPE INJECTION DEVICE AND ELECTRONIC CLIP-ON MODULE THEREFOR

CROSS REFERENCE TO RELATED APPLICATIONS

The present application is a U.S. National Phase Application pursuant to 35 U.S.C. §371 of International Application No. PCT/EP2013/052507 filed Feb. 8, 2013, which claims priority to European Patent Application No. 12155199.8 filed Feb. 13, 2012 and U.S. Provisional Patent Application No. 61/604,702 filed Feb. 29, 2012. The entire disclosure contents of these applications are herewith incorporated by reference into the present application.

FIELD OF INVENTION

The present invention relates to an apparatus for supplementing a medical device configured to eject a medicament. In particular, the present invention relates to a supplementary device for a manually operable injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

The control circuit of the medical device described in WO 2009/024562 can thus be used with a series of pre-filled disposable injection devices, but the requirement that the RFID unit with the value sensor is contained in the medicament container of the pre-filled disposable injection devices significantly increases the costs of the pre-filled disposable injection device.

It has been described, for instance in WO 2011/117212 to provide a supplementary device comprising a mating unit for releasably attaching the device to an injection device. The device includes a camera and is configured to perform optical character recognition (OCR) on captured images visible through a dosage window of the injection pen, thereby to determine a dose of medicament that has been dialed into the injection device.

SUMMARY

It is thus inter alia an object of the present invention to provide a supplementary device for a manually operable injection device.

According to a first aspect of embodiments of the present invention, there is provided a supplementary device for a manually operable injection device, the supplementary device comprising a body and a mating unit configured to releasably mount the body to the injection device in a specific position relative to an outside surface of the injection device. The mating unit may comprise a collar extending from the body which is configured to receive an injection device so that the injection device extends through the collar.

The mating unit may further comprise an engaging unit configured to engage the supplementary device with the injection device.

The engaging unit may further comprise a support member having an engaging element. The engaging element may be configured to engage in an indent on the injection device when the body is disposed in a specific position relative to an outside surface of the injection device.

The support member may be a first support member and the engaging unit may further comprise a second support member, engaging elements may be disposed at the free end of each support member, and the free ends of the support members may be biased towards each other.

Each support member may be pivotally mounted in the body about a mid-section so that the free ends of the support members may be biased away from each other to disengage the protuberances from the indents.

The collar may comprise a closure which is movable towards the body to secure the body to the injection device.

The closure may be rotatable towards the body into a secured position, and the closure may be configured to act on the support member to urge the engaging element into the indent when the closure is in its secured position so that the body is secured to the injection device.

The mating unit may further comprise a catch arrangement configured to releasably retain the closure in its secured position.

The body may have an injection device receiving channel and the axis of rotation of the closure relative to the body may extends perpendicular to the longitudinal axis of the injection device receiving channel.

The mating unit may further comprise first and second locating surfaces spaced from each other to receive an injection device therebetween. The collar may be configured to be pivoted between a first position in which an injection device is slidably receivable through the collar and a secured position in which the first and second locating surfaces are located against an outer surface of the injection device.

The engaging unit may be configured to engage with the injection device when the collar is pivoted into its secured position.

The second locating surface may be disposed between the first locating surface and the engaging unit.

The mating unit may further comprise a locating recess in the body, the locating recess being configured to mate with a locating rib on the injection device.

The supplementary device may further comprise an optical reading arrangement. The optical reading arrangement may be directed at a display of the injection device when the body is mounted to the injection device in a specific position relative to an outside surface of the injection device.

According to another aspect of embodiments of the invention, there is provided a kit comprising an injection device and a supplementary device.

Embodiments of the invention will now be described, by way of example only, with reference to the accompanying drawings.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1:
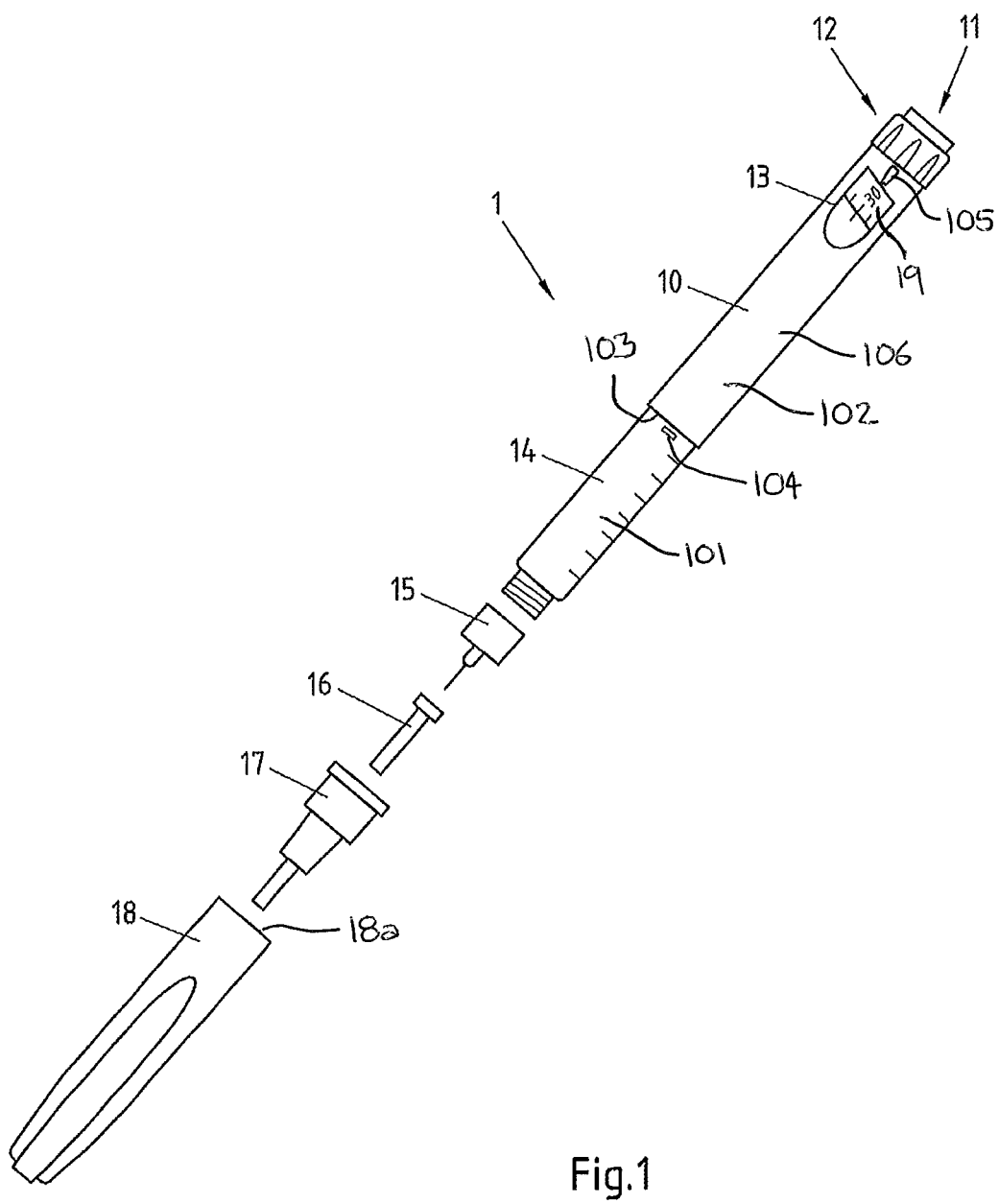
FIG. 1: an exploded view of an injection device.

FIG. 1 is an exploded view of an injection device 1, which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning a dosage knob 12, and the selected dose is then displayed via a dosage window or display 13, for instance in multiples of so-called International Units (IU), wherein one IU is the biological equivalent of about 45.5 micrograms of pure crystalline insulin (1/22 mg). An example of a selected dose displayed in dosage window or display 13 may for instance be 30 IUs, as shown in FIG. 1. It should be noted that the selected dose may equally well be displayed differently, for instance by an electronic display. It will be understood that dosage window relates to the section of the injection device through or on which the selected dosage is visible.

Turning the dosage knob 12 causes a mechanical click sound to provide acoustical feedback to a user. The numbers displayed in dosage window or display 13 are printed on a sleeve that is contained in housing 10 and mechanically interacts with a piston in insulin container 14. When needle 15 is stuck into a skin portion of a patient, and then injection button 11 is pushed, the insulin dose displayed in display 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

The housing 10 of the injection device 1 comprises a front section 101 and a rear section 102. The needle 15 is affixed to the front end of the front section 101 and the dosage knob 12 extends from the rear end of the rear section 102. The front section 101 has a smaller diameter than the rear section 102 of the injection device housing 10. A shoulder 103 is defined between the front section 101 and the rear section 102. The shoulder 103 extends circumferentially around the housing 10.

The cap 18 extends over the front section 101. The cap 18 covers the front section 101 and a lip 18a of the cap 18 locates against the shoulder 103.

A cap retaining ridge 104 is formed on the outer surface of the front section 101 of the housing 10 of the injection device 1. The cap retaining ridge 104 is disposed proximate to, but spaced from, the shoulder 103. The ridge 104 extends diametrically about the front section 101. The ridge 104 locates over one or more retaining elements (not shown) formed on the inner surface of the cap 18 to retain the cap 18 in position over the front section 101. Alternatively, the cap retaining ridge 104 locates in a corresponding diametrically extending recess (not shown) formed on the inner surface of the cap 18.

The injection device 1 further comprises additional elements. A rib 105 protrudes from an outer surface 106 of the injection device 1. The rib 105 acts as an alignment element for locating the body in a specific position relative to the outer surface 106 of the injection device 1. The rib 105 upstands from the outer surface 106 of the injection device 1 between the dosage display 13 and the dosage knob 12. The dosage knob 12 is disposed on the rear section 102 of the injection device housing 10. The rib 105 is elongate and extends parallel to the longitudinal axis of the injection device 1.

Left and right indents 107 (refer to FIG. 8) are formed in the outer surface 106 of the injection device 1. The two indents 107 are formed in the rear section 102. Each indent 107 is formed proximate to the rear end of the injection device housing 10. The indents 107 are formed generally diametrically opposite to each other on left and right sides of the injection device 1. The indents 107 have chamfered sides.

Figure 2A:
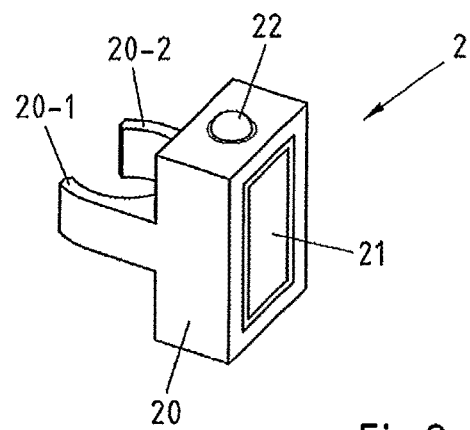
FIG. 2a: a schematic illustration of a supplementary device to be releasably attached to the injection device of FIG. 1 according to an embodiment of the present invention.

FIG. 2a is a schematic illustration of an embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1, for instance when the injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage display 13 of injection device 1 is obstructed by supplementary device 2 when attached to injection device 1.

Supplementary device 2 further comprises three user input transducers, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
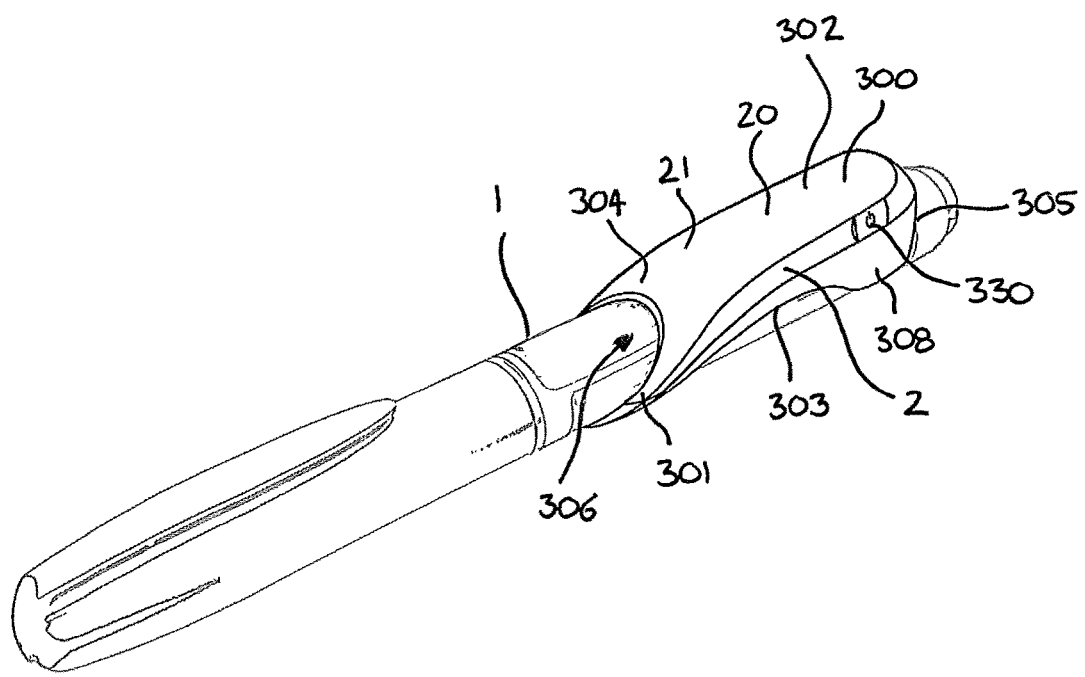
FIG. 2b: a perspective view of the supplementary device of FIG. 2a releasably attached to the injection device of FIG. 1.

FIG. 2b shows a view of the supplementary device 2 with the arrangement of the mating unit and housing shown in greater detail. The supplementary device 2 is shown mounted to the injection device 1 in FIG. 2b.

The housing 20 of the supplementary device 2 has a body 300 and a collar 301. The body 300 is elongate and the display unit 21 is disposed on an upper side 302 of the body 300. The collar 301 extends from a lower side 303 of the body 300. The body 300 has a front end 304 and a rear end 305. The collar 301 extends from the front end 304. The collar 301 extends from the body 300 at an acute angle to the longitudinal axis of the elongate body 300.

The collar 301 has an aperture 306 formed therethrough. The collar 301 is configured to receive the injection device 1 through the aperture 306. A channel 307 (refer to FIG. 11) is formed in the lower side 303 of the body 300. The channel 307 is elongate and extends between the front end 304 and the rear end 305 of the body 300.

Two wings 308, acting as protective walls, extend downwardly from the lower side 303 of the body 300. The wings 308 are spaced from each other and distend from either side of the channel 307. Therefore, the injection device 1 is receivable between the wings 308. The wings 308 are disposed at the rear end 305 of the body 300, at an opposite end of the body 300 to the collar 301.

The collar 301 and channel 307 form part of an alignment arrangement or alignment unit. The alignment unit is configured to locate the body in a specific position relative to the outside surface 106 of the injection device 1. The alignment unit forms part of the mating unit configured to embrace the housing 10 of injection device 1 to maintain the supplementary device in a specific position on the injection device 1.

The supplementary device 2 further comprises an engaging unit or arrangement configured to releasably mount the body to the injection device 1. The collar 301 also forms part of the engaging unit. The engagement unit forms part of the mating unit.

The features that contribute to correct alignment of the supplementary device 2 on the injection device 1 can be termed an alignment arrangement or alignment unit. The features that contribute to engagement of the supplementary device 2 to the injection device 1 can be termed an engaging unit or engaging arrangement.

Figure 3A:
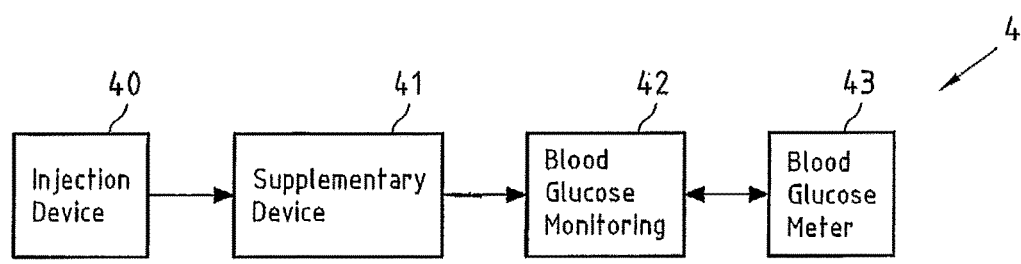
FIGS. 3A and 3b: possible distributions of functions among devices when using a supplementary device (such as the supplementary devices of FIGS. 2a and 2b) together with an injection device.
Figure 3B:
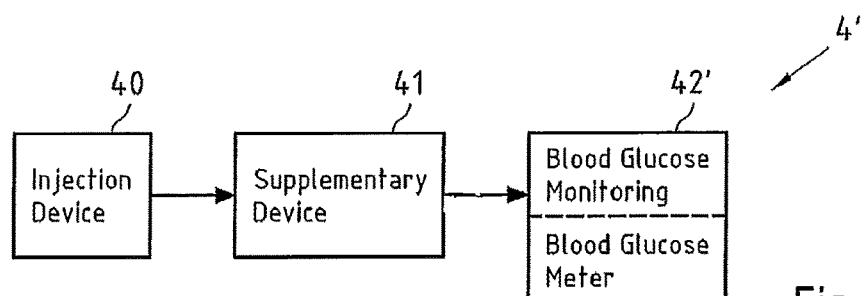

FIGS. 3A and 3b show possible distributions of functions among devices when using a supplementary device (such as the supplementary devices of FIGS. 2a and 2b) together with an injection device.

In constellation 4 of FIG. 3a, the supplementary device 41 (such as the supplementary devices of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as a desktop computer, personal digital assistant, mobile phone, tablet computer, notebook, netbook or ultrabook) keeps a record of the injections a patient has received so far (based on the ejected doses, for instance by assuming that the ejected doses and the injected doses are the same, or by determining the injected doses based on the ejected doses, for instance by assuming that a pre-defined percentage of the ejected dose is not completely received by the patient). Blood glucose monitoring system 42 may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42. Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionalities of injection device 40 and supplementary device 41 of FIG. 3a are not affected by this modification. Also the functionality of blood glucose monitoring system 42 and blood glucose meter 43 combined into blood glucose monitoring system 42' are basically unchanged, apart from the fact that both are now comprised in the same device, so that external wired or wireless communication between these devices is no longer necessary. However, communication between blood glucose monitoring system 42 and blood glucose meter 43 takes place within system 42'.

Figure 4:
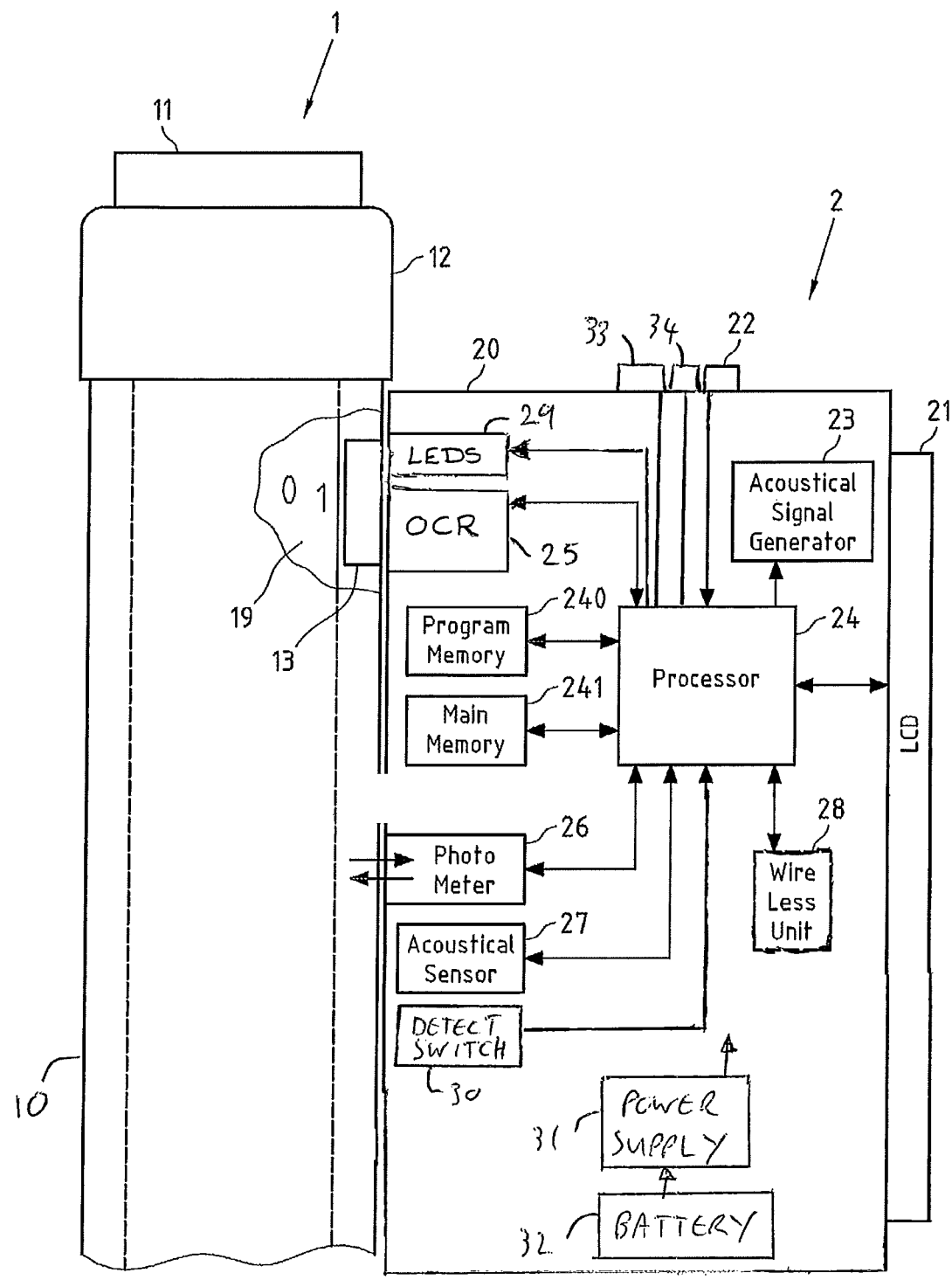
FIG. 4: a schematic view of the supplementary device of FIG. 2 in a state where it is mounted to the injection device of FIG. 1.

FIG. 4 shows a schematic view of the supplementary device 2 of FIG. 2a in a state where it is attached to injection device 1 of FIG. 1.

With the housing 20 of supplementary device 2, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In an example embodiment, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. The buttons 22, 33, 34 may be any suitable form of user input transducers, for instance mechanical switches, capacitive sensors or other touch sensors.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage display 13, in which a currently selected dose is displayed (by way of numbers printed on the sleeve 19 contained in injection device 1, which numbers are visible through the dosage display 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage display 13, in which a currently selected dose is displayed. A diffuser may be used in front of the light-sources, for instance a diffuser made from a piece of acrylic glass. Furthermore, the optical sensor may comprise a lens (e.g. an aspheric lens) leading to a magnification (e.g. a magnification of more than 3:1).

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through an opening or window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage display 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1.

A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 5A:
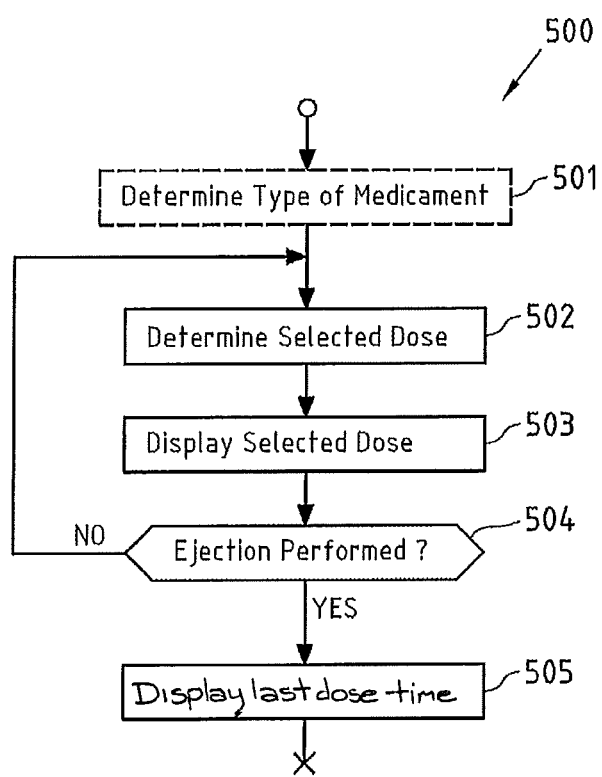
FIG. 5a: a flowchart of a method used in various embodiments.
Figure 5B:
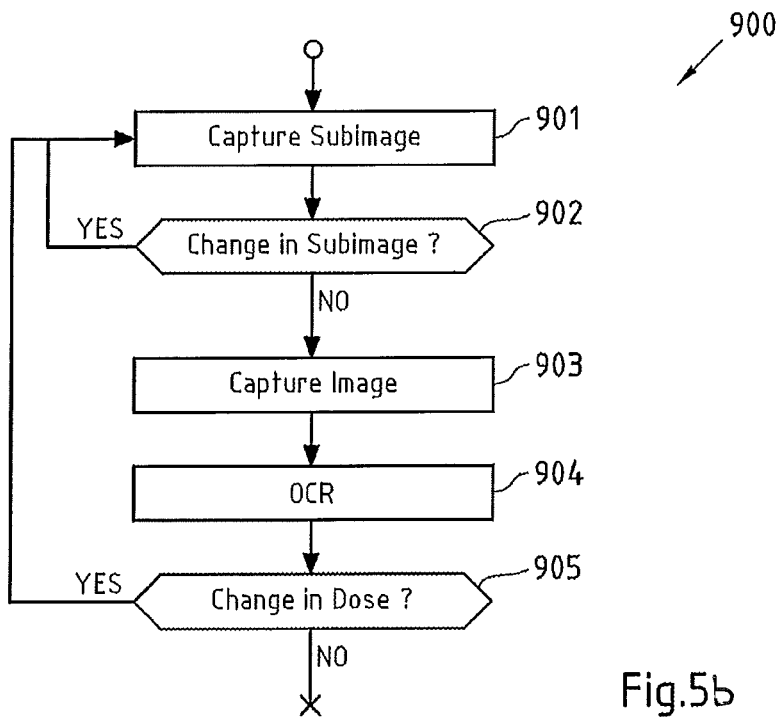
FIG. 5b: a flowchart of a further method used in a various embodiments.
Figure 5C:
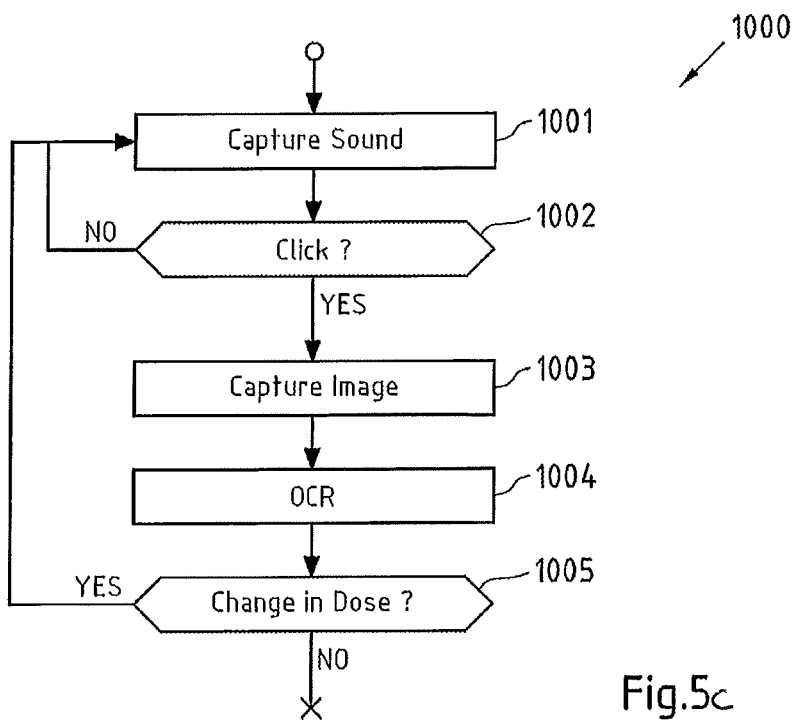
FIG. 5c: a flowchart of another method used in various embodiments.

FIGS. 5a-5c are flowcharts of embodiments of methods according to the present invention. These methods may for instance be performed by processor 24 of supplementary device 2 (see FIGS. 2b and 4), but also by a processor of supplementary device 3 of FIG. 2b, and may for instance be stored in program memory 240 of supplementary device 2, which may for instance take the shape of tangible storage medium 60 of FIG. 6.

FIG. 5a shows method steps that are performed in scenarios as shown in FIGS. 3a and 3b, where information read by supplementary device 41 from injection device 40 is provided to blood glucose monitoring system 42 or 42' without receiving information back from blood glucose monitoring system 42 or 42'.

The flowchart 500 starts for instance when the supplementary device is turned on or is otherwise activated. In a step 501, a type of medicament, for example insulin, provided by the injection device is determined, for instance based on colour recognition or based on recognition of a code printed on injection device or a component thereof as already described above. Detection of the type of medicament may not be necessary if a patient always takes the same type of medicament and only uses an injection device with this single type of medicament. Furthermore, determination of the type of medicament may be ensured otherwise (e.g. by the key-recess pair shown in FIG. 4 that the supplementary device is only useable with one specific injection device, which may then only provide this single type of medicament).

In a step 502, a currently selected dose is determined, for instance by OCR of information shown on a dosage display of injection device as described above. This information is then displayed to a user of the injection device in a step 503.

In a step 504, it is checked if an ejection has taken place, for instance by sound recognition as described above. Therein, a prime shot may be differentiated from an actual injection (into a creature) either based on respectively different sounds produced by the injection device and/or based on the ejected dose (e.g. a small dose, for instance less than a pre-defined amount of units, e.g. 4 or 3 units, may be considered to belong to a prime shot, whereas larger doses are considered to belong to an actual injection).

If an ejection has taken place, the determined data, i.e. the selected dose and—if applicable—the type of medicament (e.g. insulin), is stored in the main memory 241, from where it may later be transmitted to another device, for instance a blood glucose monitoring system. If a differentiation has been made concerning the nature of the ejection, for instance if the ejection was performed as a prime shot or as an actual injection, this information may also be stored in the main memory 241, and possibly later transmitted. In the case of an injection having been performed, at step 505 the dose is displayed on the display 21. Also displayed is a time since the last injection which, immediately after injection, is 0 or 1 minute. The time since last dose may be displayed intermittently. For instance, it may be displayed alternately with the name or other identification of the medicament that was injected, e.g. Apidra or Lantus.

If ejection was not performed at step 504, steps 502 and 503 are repeated.

After display of the delivered dose and time data, the flowchart 500 terminates.

FIG. 5c shows in more detail exemplary method steps that are performed when the selected dose is determined based on the use of optical sensors only. For instance, these steps may be performed in step 502 of FIG. 5a.

In a step 901, a sub-image is captured by an optical sensor such as optical sensor 25 of supplementary device 2. The captured sub-image is for instance an image of at least a part of the dosage window 13 of injection device 1, in which a currently selected dose is displayed (e.g. by way of numbers and/or a scale printed on the sleeve 19 of injection device 1, which is visible through the dosage window 13). For instance, the captured sub-image may have a low resolution and/or may only show a part of the part of sleeve 19 which is visible through dosage window 13. For instance, the captured sub-image either shows the numbers or the scale printed on the part of sleeve 19 of injection device 1 which is visible through dosage window 13. After capturing an image, it is, for instance, further processed as follows:

Division by a previously captured background image;

Binning of the image(s) to reduce the number of pixels for further evaluations;

Normalization of the image(s) to reduce intensity variations in the illumination;

Sheering of the image(s); and/or

Binarization of the image(s) by comparing to a fixed threshold.

Several or all of these steps may be omitted if applicable, for instance if a sufficiently large optical sensor (e.g. a sensor with sufficiently large pixels) is used.

In a step 902, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns. Steps 901 and 902 may correspond to a detection of a change in the captured image.

If it is determined in step 902 that there is a change in the sub-image, step 901 is repeated. Otherwise in a step 903, an image is captured by an optical sensor such as optical sensor 25 of supplementary device 2. The captured image is for instance an image of the dosage window 13 of injection device 1, in which a currently selected dose is displayed (e.g. by way of numbers and/or a scale printed on the sleeve 19 of injection device 1, which is visible through the dosage window 13). For instance, the captured image may have a resolution being higher than the resolution of the captured sub-image. The captured image at least shows the numbers printed on the sleeve 19 of injection device 1 which are visible through the dosage window 13.

In a step 904, optical character recognition (OCR) is performed on the image captured in step 903 in order to recognize the numbers printed on the sleeve 19 of injection device 1 and visible through the dosage window 13, because these numbers correspond to the (currently) selected dose. In accord to the recognized numbers, the selected dose is determined, for instance by setting a value representing the selected dose to the recognized numbers.

In a step 905, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

FIG. 5c shows in more detail method steps that are performed when the selected dose is determined based on the use of acoustical and optical sensors. For instance, these steps may be performed in step 502 of FIG. 5a.

In a step 1001, a sound is captured by an acoustical sensor such as acoustical sensor 27 of supplementary device 2.

In a step 1002, it is determined whether or not the captured sound is a click sound. The captured sound may for instance be a click sound that occurs when a dose is dialed by turning dosage knob 12 of injection device 1 and/or when a dose is ejected/injected by pressing injection button 11, and/or when a prime shot is performed. If the captured sound is not a click sound, step 1001 is repeated. Otherwise in a step 1003, an image is captured by an optical sensor such as optical sensor 25 of supplementary device 2. Step 1003 corresponds to step 903 of flowchart 900.

In a step 1004, an OCR is performed on the image captured in step 1003. Step 1004 corresponds to step 904 of flowchart 900.

In a step 1005, it is determined whether or not there is a change in the determined selected dose and, optionally, whether or not the determined selected dose does not equal zero. Step 1005 corresponds to step 905 of flowchart 900.

There might be a slight advantage of the acoustic approach shown in FIG. 5c when it comes to power consumption of the supplementary device, because permanently capturing images or sub-images as shown in FIG. 5b typically is more power consuming than listening to an acoustical sensor such as a microphone.

Figure 6:
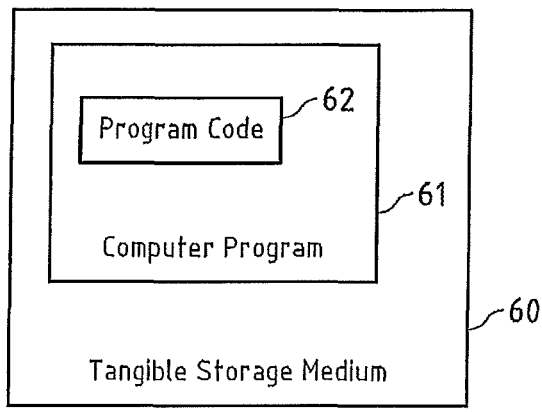
FIG. 6: a schematic illustration of a tangible storage medium 60 according to an embodiment of the present invention.

FIG. 6 is a schematic illustration of a tangible storage medium 60 (a computer program product) that comprises a computer program 61 with program code 62 according to aspects of the present invention. This program code may for instance be executed by processors contained in the supplementary device, for instance processor 24 of supplementary device 2 of FIGS. 2a and 4. For instance, storage medium 60 may represent program memory 240 of supplementary device 2 of FIG. 4. Storage medium 60 may be a fixed memory, or a removable memory, such as for instance a memory stick or card.

Figure 7:
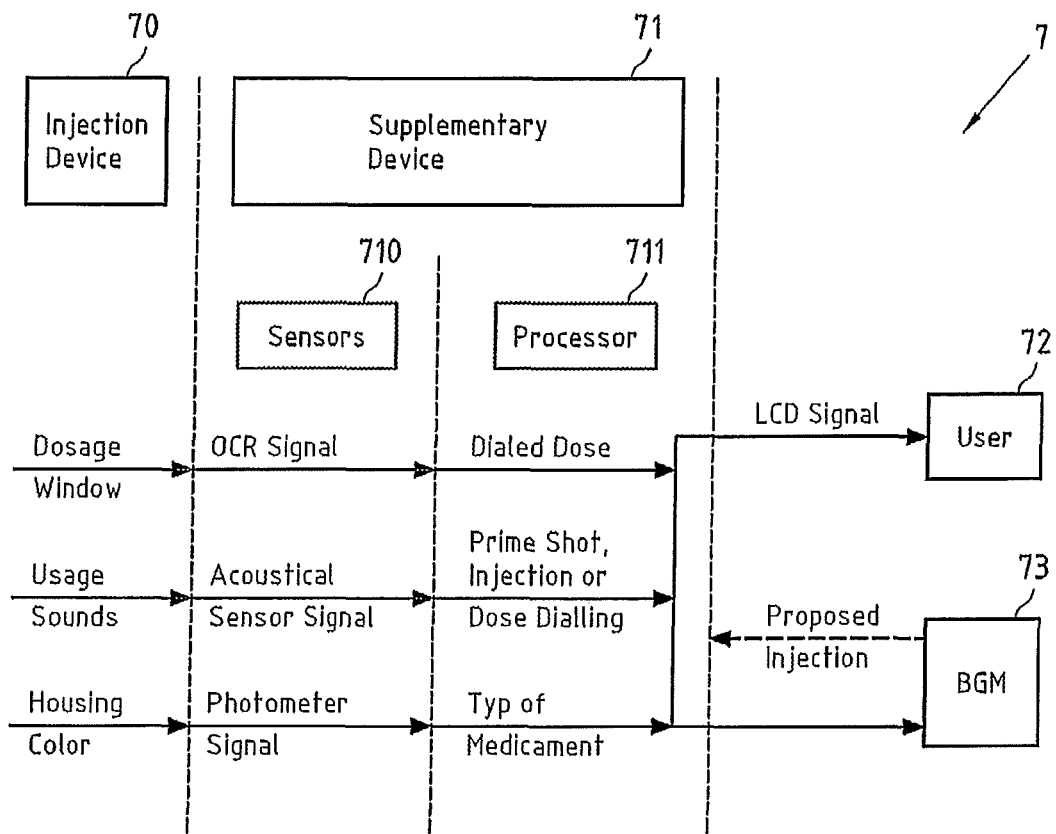
FIG. 7: an information sequence chart that illustrates an information flow between various devices according to embodiments of the invention.

Finally, FIG. 7 is an information sequence chart 7 that illustrates the flow of information between various devices (e.g. the injection device 1 and the supplementary device 2 of FIG. 4 in a scenario as depicted in FIG. 3a or 3b) according to an embodiment of the present invention. A condition and/or use of injection device 70 affects an appearance of its dosage window, sounds generated by injection device 70 and a colour of the housing. This information is transformed by sensors 710 of supplementary device 71 into an OCR signal, an acoustic sensor signal and a photometer signal, respectively, which are in turn transformed into information on the dialed dose, on an injection/dialing operation and on the type of insulin by a processor 711 of supplementary device 71, respectively. This information is then provided by supplementary device 70 to a blood glucose monitoring system 73. Some or all of this information is displayed to a user 72 via the display 21.

As described in detail above, embodiments of the present invention allow connection of a standard injection device, in particular an insulin device, with a blood glucose monitoring system in a useful and productive way.

Embodiments of the present invention introduce a supplementary device to allow for this connection, assuming the blood glucose monitoring system has wireless or other communication capabilities.

The benefits from the connection between the blood glucose monitoring and an insulin injection device are inter alia the reduction of mistakes by the user of the injection device and a reduction of handling steps—no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the supplementary device to the pen by way of the mating unit, as will be described in detail hereinafter. The supplementary device reads out the injected dose. It may also transfer it to a blood glucose monitoring system with insulin titration capabilities. For patients taking multiple insulins, the supplementary device recognizes the device structure to the insulin type and may also transmit this piece of information to the blood glucose monitoring system.

The mating unit for releasably mounting the supplementary device to the injection device in a specific position relative to an outside surface of the injection device will now be described in detail.

The correct alignment of the supplementary device 2 on the injection device 1 ensures that the OCR reader 25 is correctly aligned with the dosage window 13. Correct alignment allows correct operation and reliable readings. Ensuring that there can be correct alignment between the supplementary device 2 and the injection device 1 in use allows a simpler design for the OCR reader 25, in particular because it does not need to be designed to be able to accommodate different alignments between the devices 1, 2.

Figure 8:
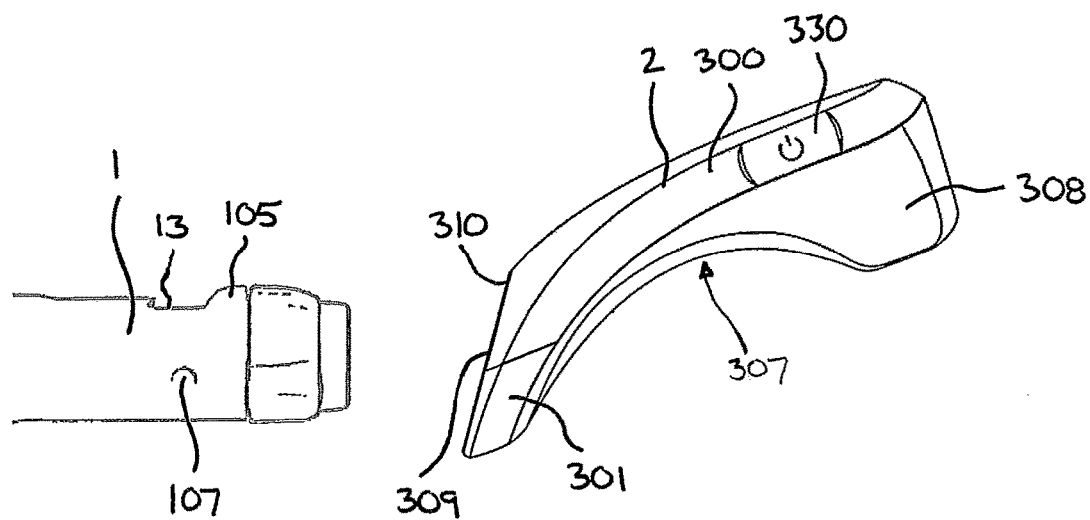
FIG. 8: a perspective view of the supplementary device shown in FIG. 2b orientated to be mounted to the injection device of FIG. 1.

Referring to FIG. 8, the supplementary device 2 is shown prior to mounting the supplementary device 2 on the injection device 1. In FIG. 8, the supplementary device 2 is shown orientated relative to the rear section 102 of the housing 10 of the injection device 1 so that the rear section 102 is receivable through the aperture 306 formed in the collar 301.

The housing 20 of the supplementary device 2 comprises the body 300 and the collar 301. The elongate body 300 has a longitudinal axis, with the collar 301 distending downwardly from the front end 304 of the body 300.

The channel 307 (refer to FIGS. 10 and 11) formed in the lower side 303 of the body 300 extends from the aperture 306 formed in the collar 301. Therefore, an upper portion of the aperture 306 forms part of the elongate channel extending between the front end and the rear end of the housing 20.

The aperture 306 has a front opening 309. The front opening 309 is formed in a front face 310 of the housing 20. The front face 310 may be planar. The edge of the front opening 309 is defined on a plane extending at an angle to the longitudinal axis of the elongate body 300. The front opening 309 has an elliptical shape. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. It will be understood that the rear section 102 of the injection device 1 is receivable through the opening 309 so that it extends through the aperture 306.

Figure 10:
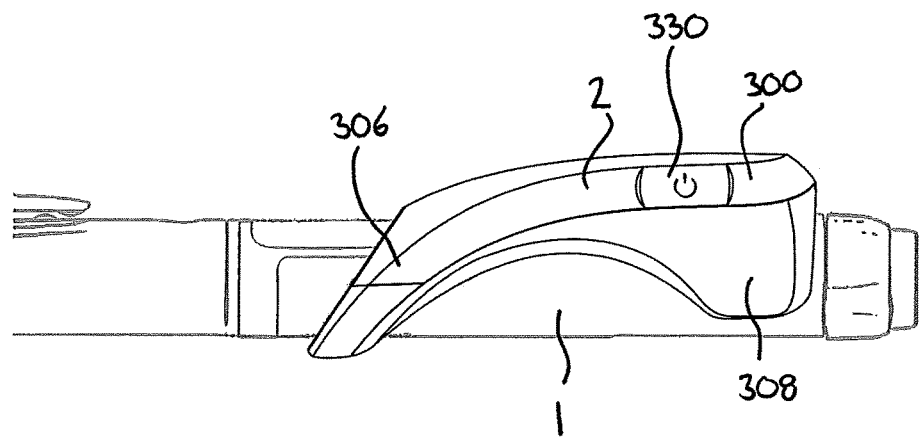
FIG. 10: a side view of the supplementary device shown in FIG. 2b releasably attached to the injection device of FIG. 1.
Figure 11:
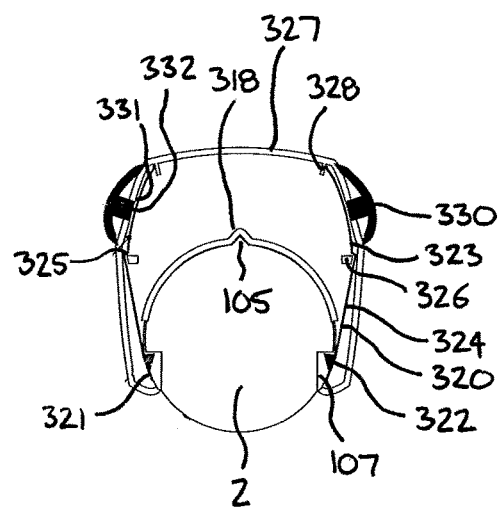
FIG. 11: a cross-sectional rear view of the supplementary device shown in FIG. 2b releasably attached to the injection device of FIG. 1 with resilient arms of a fixing unit in an engaged position with the injection device.
Figure 12:
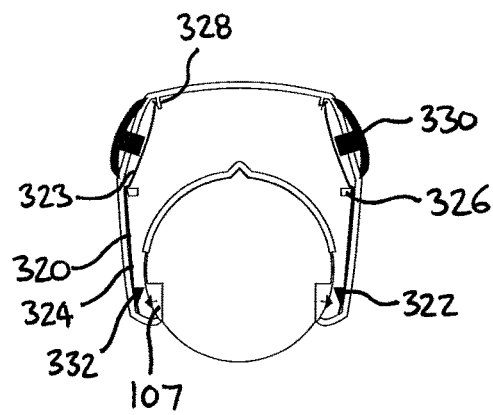
FIG. 12: a cross-sectional rear view of the supplementary device shown in FIG. 2b releasably attached to the injection device of FIG. 1 with resilient arms of a fixing unit in a disengaged position with the injection device.
Figure 13:
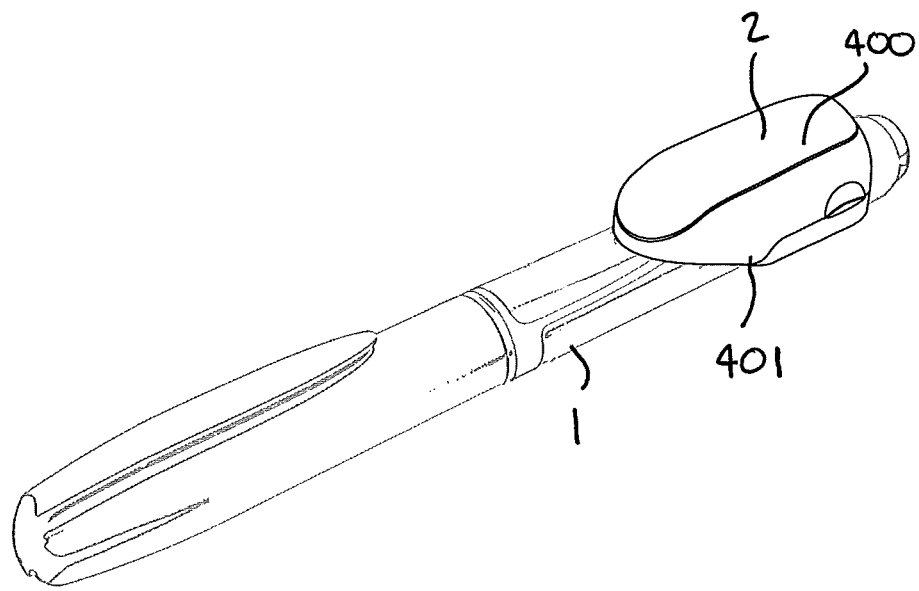
FIG. 13: a perspective view of another embodiment of the supplementary device releasably attached to the injection device of FIG. 1.

The channel 307 is shown in FIGS. 10 to 12. The channel 307 has a base 312. The base 312 of the channel 307 is arcuate in cross-section. The base 312 extends parallel to the longitudinal axis of the body 300. The shape of the base 312 corresponds to the outer surface of the rear section 102 of the injection device 1. Therefore, the rear section 102 of the injection device is receivable therein and the outer surface of the injection device 1 locates against the channel base 312. The optical sensor 25 is embedded in the channel base 312 to face into the channel 312.

The collar 301 defines an upper part 314 and a lower part 315. The upper part 314 is integrally formed with the body 300 and thus extends from the base 312 of the channel 307. The lower part 315 opposes, but is at least partially offset from, the upper part 314. In the present embodiment, the upper part 314 is defined by the upper half of the inner surface of the collar 301 and the lower part 315 is defined by the lower half of the inner surface of the collar 301. The inner surface of the collar 301 defines a cylinder, with the base 312 of the channel 307 extending from the cylindrical surface. Therefore, the arcuate base of the channel 307 and the inner cylindrical surface of the collar are formed to arc about the same longitudinal axis.

A lower locating surface 317 is defined on the lower part 315 of the collar 301. An upper locating surface 316 is defined on the upper part 314 of the collar 301. The upper and lower locating surfaces oppose each other. When the injection device is received through the aperture, the upper and lower locating surfaces 316, 317 are configured to locate against the outer surface of the injection device 1. the locating surfaces 316, 317 are brought into contact with the injection device 1 by rotating the supplementary device 2 about an axis extending perpendicular to the major axis of the opening 309 so that the upper and lower locating surfaces are moved towards the outer surface of the injection device 1. The central axis of the cylindrical aperture extending through the collar is brought into co-axial alignment with the longitudinal axis of the injection device 1.

In the present embodiment, the base 312 of the channel extends co-planer with the upper part of the collar 301. Therefore, the base 312 of the channel also locates against the outer surface of the injection device 1 when the supplementary device 2 is rotated about an axis extending perpendicular to the major axis of the opening 309 so that the upper and lower locating surfaces are moved to lie against the outer surface of the injection device 1. Therefore, it will be understood that the upper locating surface may be formed by the upper part of the collar, or by the base 312 of the channel 307. Alternatively, the lower locating surface is formed on one or more locating elements protruding into the aperture from the lower part of the collar. Similarly, the upper locating surface is formed on one or more locating elements protruding into the aperture or the injection device receiving channel.

A rib receiving recess 318 (refer to FIGS. 11 and 12) is formed in the base 312 of the channel 307. The rib receiving recess 318 is dimensioned to receive the rib 105 protruding from the outer surface 106 of the injection device 1. The rib receiving recess 318 is dimensioned so as to correspond closely to the shape and size of the locating rib 105 that is present on the injection pen 1. The rib receiving recess 318 is slightly larger than the locating rib 105 so as to ensure that the locating rib 105 can be easily located within the recess. Therefore, the rib 105 acts as an alignment element for locating the body in a specific position relative to the outer surface 106 of the injection device 1 when the rib 105 is received in the rib receiving recess 318. The rib receiving recess 318 therefore aids the correct alignment and orientation of the body 300 on the injection device 1.

The rib receiving recess 318 is formed at the end of the supplementary device 2 that is closest to the dosage knob 12 when the supplementary device 2 is fitted to the injection device 1.

Left and right arms 320, acting as support members, extend below the injection device receiving channel 307 on left and right sides of the body 300. As shown in FIGS. 11 and 12, a lower part 324 of each arm 320 depends substantially vertically from the lower side of the body 300 of the supplementary device 2. Therefore, the arms 320 extend either side of the injection device receiving channel 307 and are spaced from each other.

The left arm 320 has a left protuberance 322 disposed at a free end 321 of the lower part 324. The right arm 320 also has a right protuberance 322 disposed at a free end 321 of the lower part 324. Each protuberance 322 acts as an engaging element to engage in the indents 107 formed in the outer surface of the rear section 102 of the injection device 1. The protuberance 322 on the left arm 320 is configured to be received in the left indent 107. The protuberance 322 on the right arm 320 is configured to be received in the left indent 107. The protuberances 322 are shaped to correspond to the shapes of the indents 107 respectively. In this way, the protuberances 322 fit within the corresponding indents 107 respectively when the supplementary device 2 is correctly positioned on the injection device 1. The external dimensions of the protuberances 322 are slightly smaller than the internal dimensions of the indents 107 so as to ensure that the protuberances 322 fit within their respective indent.

In the present embodiments, the right protuberance 322 is shaped to correspond closely to the shape of the right indent 107. In this way, the right protuberance 322 fits snugly within the right indent 107 when the supplementary device 2 is correctly positioned on the injection pen 1. The left protuberance 322 is shaped similarly to the right protuberance 322, although it is less tall. Put another way, it is like the right protuberance 322 but with the top part is missing or cut off. This is the reason for the end face of the left protuberance 322 having a larger area than the right protuberance 322. The different sizes for the protuberances 322 helps the protuberances find engagement within the indents 107. The right protuberance 322 can be considered to be a master to the left protuberance 322, which is a slave.

Each arm 320 has an upper part 323 and a lower part 324. A step 325 is formed at a mid section of each arm 320, with the upper part 323 depending from one side of the step 325 and the lower part 324 depending from the other side. The protuberance 322 is formed at the free end of the lower part 324. The lower part 324 extends from the step 325 at an angle to the upper part 323.

A support element 326 is disposed in the left side of the body 300. Another support element 326 is disposed in the right side of the body 300. Each support element 326 is disposed in the body 300 and spaced from an outer shell 327 of the body 300 to define a gap. The left arm 320 is received in a left side of the body 300. The right arm 320 is received in a right side of the body 300. The arms 320 are disposed behind the wings 308 that depend from the body 300. The wings 308 may be formed from a transparent material. This allows a user to be able to view the locations of the arms 320 relative to the indents 107, which may help the user to locate the supplementary device 2 correctly on the injection device 1. As can be seen from FIG. 11, the wings, or protective walls 308, extend slightly further in a downwards direction than the arms. The left arm 320 extends through the gap formed in the left side of the body 300 and the right arm 320 extends through the gap on the right side of the body 300. The step 325 formed at the mid-section of each arm 320 locates against the corresponding support element 326. The step 325 locates each arm 320 so that the lower part 324 extends below the support element 326. The end of the upper part 323 of each arm 320 locates against a tab 328 extending from an inner surface of the body outer shell 327. The upper part 323 of each arm 320 is therefore retained in position in the body 300 and extends between the support element 326 and the tab 328.

The distance between each support element 326 and tab 328 is slightly less than the length of the upper part 323 of each arm 320. Therefore, when the upper part 323 of each arm 320 is disposed between the corresponding element 326 and the tab 328, the upper part 323 of each arm 320 is deformed to have an arcuate shape. Each arm 320 is resilient. The upper part 323 bows into a convex shape towards the outer shell of the body 300. Therefore, the step 325 is biased against the support element 326 and the free end of the upper part 323 is biased against the tab 328. The upper part 323 of each arm 320 between the free end and the step is urged towards the outer shell 327.

The lower part 324 of each arm 320 extends from the upper part 323 and through the gap defined between the support element 326 and the outer shell 327. The lower parts 324 of the arms 320 are splayed towards each other, extending from the support element 326. The effect of the resilience of the upper part 323 of each arm 320 is to bias the lower part 324 of each arm 320 into a certain position. The position into which the lower part 324 of each arm 320 is initially located is such that the distance between the innermost surfaces of the protuberances 322 is slightly less than the distance between the bottoms of the indents 107. The effect of the bias of each arm 320 is to resist movement of the protuberances 322 and the lower parts 324 of the arms 320 away from one another.

The arms 320, acting as support members, are restrained from moving in a direction along the longitudinal axis of the elongate body 300. This assists in maintaining the supplementary device 2 in the correct location after engagement of the supplementary device on the injection pen 1 even in the presence of forces acting to move the supplementary device 2 along the longitudinal axis of the injection pen 1. The arms 320 can be termed support members because they support the protuberances.

Left and right buttons 330 are mounted on the left and right sides of the body 300. An aperture 331 is formed through the outer shell 327 on each side of the body 300. A protrusion, acting as an actuating element 332, is formed on the rear side of each button 330 and extends through the corresponding aperture 331 to act on the upper part 323 of the corresponding arm 320 and apply a biasing force thereon.

When one of the buttons 330 is pressed inwardly by a user the actuating element 332 of each button 330 is biased inwardly. The actuating element 332 urges against the convex surface of the upper part 323 of the corresponding arm 320. The upper part 323 then deforms under the force applied by the actuating element 332. The support element 324 acts as a fulcrum and the arm 320 is urged to pivot about the support element. The distal end of the upper part 323 is prevented from moving by the tab 328 against which the upper part 323 is located. However, the free end 321 of the lower part 324 is free to move outwardly and so the lower part 324 pivots about the support element 324.

When both buttons are pressed, the lower parts 324 of the two arms 320 are urged to rotate about their respective support elements 324. Therefore, the free ends 321 of the arm lower parts 324 are urged away from each other. The release of the pressing force on each button releases the biasing force acting on the upper part 323 of each arm and so the lower part of each arm is urged to return to its neutral position due to the resilience of the arms 320.

As is shown in FIG. 8, the supplementary device 2 is initially located with respect to the injection pen 1 such that the opening 309 to the aperture 306 in the collar 301 is aligned with the rear end of the injection device 1. The body 300 is orientated so that the longitudinal axis of the injection device receiving channel 307 is inclined with respect to the longitudinal axis of the injection device 1.

Figure 9:
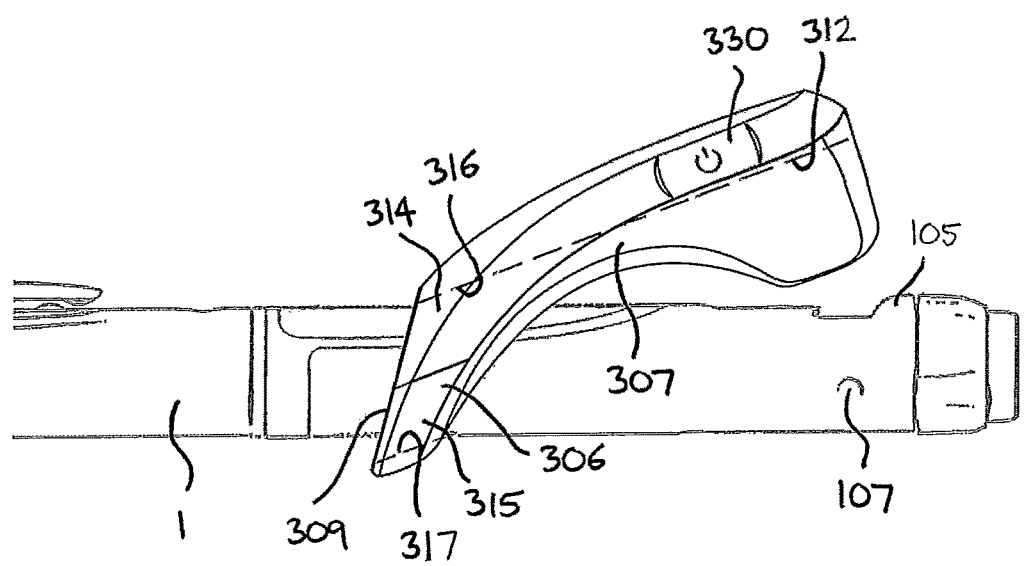
FIG. 9: a perspective view of the supplementary device shown in FIG. 2b with the injection device of FIG. 1 received through a collar of the supplementary device.

The collar 301 is then slid over the rear section 102 of the injection device 1, as shown in FIG. 9. The width of the front opening 309 at its minor axis or conjugate diameter corresponds to or is slightly greater than the diameter of the rear section 102 of the injection device 1. The width of the front opening 309 at its major axis or transverse diameter is greater than the diameter of the rear section 102 of the injection device 1. Therefore, the rear section 102 of the injection device 1 is received through the aperture 306 of the collar 301.

In order to locate the supplementary device 2 on the injection device 1, the supplementary device 2 is rotated relative to the injection device 1 about an axis extending perpendicular to the major axis of the opening 309. The longitudinal axes of the injection device 1 and the injection device receiving channel 307 are rotated towards each other. Furthermore, the upper and lower locating surfaces 316, 317 are moved towards the outer surface of the injection device 1.

As the supplementary device 2 and injection device 1 are rotated relative to each other the free ends 321 of the right and left arms 320, in particular the protuberances 322, brought into contact with the outer surface of the injection device housing 10. The protuberances 322 here contact the housing to the left and right sides of the display window 13.

In order to engage the supplementary device 2 with the injection device 1, the user first arranges the supplementary device 2 with respect to the injection device 1 as shown in FIG. 9, and then applies a further force downwards on the supplementary device 2 while at the same time applying a force upwards on the injection device 1. Therefore, the supplementary device 2 and injection device are urged to rotate relative to each other about the collar 301. A biasing force is therefore applied to the protuberances 322 by the outer surface of the rear section 102. As the injection device 1 and the supplementary device 2 are urged to move closer together, the biasing force results in the arms being urged away from each other. The lower part 324 of each arm 322 is urged to deflect outwardly, and to pivot about the corresponding support element 326. However, the upper part 323 of each arm is prevented from pivoting by the corresponding tab. This causes a reaction force to be applied by the lower part 324 of each arm due to the resilience of each arm 320, which resists entry of the injection device 1 into the injection device receiving channel 307. However, as the supplementary device 2 is further rotated over the injection device 1, the protuberances 322 become aligned with the left and right indent 107 and, due to the resilience of the arms 320, engage with the indents 107.

Referring to FIG. 10, as the supplementary device 2 is further rotated to engage the protuberances 322 in the indents 107, the rear section 2 of the injection device 1 is received in the injection device receiving channel 207. The lower locating surface 317 of the collar 301 is urged into contact with a lower side of the outer surface of the injection device 1 and the upper locating surface 316 is urged into contact with an opposing side of the outer surface of the injection device 1. Once the protuberances 322 engage in the indents 107, there is significant resistance to further movement of the supplementary device 2 relative to the injection device 1, due in part to the lower and upper locating surfaces 316, 317 abutting the outer surface of the injection device. The upper and lower locating surfaces 316, 317 are partially offset from each other, with the upper locating surface 317 being disposed between the lower locating surface and the protuberances 322. Movement of the supplementary device 2 relative to the injection device 1 in the opposite direction is restricted by the protuberances 322 being engaged in the indents 107. The injection device 1 also locates against the base 312 of the channel 307.

It will be understood that the body 300 is mated to the injection device 1 by the collar 301 extending circumferentially around the injection device 1 at a front end of the body 300, and the protuberances 322 engaging in the indents 107 at the rear end of the body 300.

In the event that the user places the supplementary device 2 onto the injection pen 1 at a location such that the supplementary device 2 is rotated slightly about its longitudinal axis relative to its desired position, the rib 105 will not be received in the rib receiving recess 318 in the body 300. In this case, the supplementary device 2 is prevented from being located fully over the injection pen 1 by the rib 105 resting against the base 312 of the channel 307, spaced from the correct location within the rib receiving recess 318. Furthermore, the protuberances 322 will be urged against the outer surface of the rear section 102 of the injection device 1, but will not locate in the corresponding indents 107. A user would know that the supplementary device 2 had not mated correctly with the injection pen 1 because they would not have received any haptic feedback from the mating of the protuberances 322 with the indents 107. They would also notice that the rear end of the supplementary device was separated from the injection device 1. To correctly locate the supplementary device 2 in position with respect to the injection device 1, a user can simply rotate the supplementary device 2 relative to the injection device 1 about the longitudinal axis of the injection device 1. As the supplementary device 2 and the injection device 1 move relative to one another, the locating rib and the rib receiving recess 318 become aligned with each other. At this point the protuberances 322 also align with the indents 107 and engage therewith. Haptic feedback is therefore provided by the mating of the protuberances 322 with the indents 107 and the user can determine that the supplementary device 2 and the injection device 1 are properly located with respect to one another.

Similarly, if the supplementary device 2 is not correctly aligned with the injection device 1 in a longitudinal direction, the rib 105 and rib receiving recess 318 will not be aligned and the rib will not locate in the recess. Furthermore, the protuberances 322 will be offset from the indents 107. Relative movement of the supplementary device 2 and the injection device 1 in a direction along the longitudinal axis of the injection device 1 will cause the rib to locate in the recess and the protuberances to locate in the indents 107. At this point, the supplementary device 2 and the injection device 1 are fully engaged with one another.

Once the protuberances 322 are engaged in the indents 107, the injection device 1 is fully located within the injection device receiving channel 307 as shown in FIGS. 11 and 12. Here, the outermost surface of the display window 13 is aligned with a lowermost surface of the upper part of the supplementary device 2. The supplementary device 2 is shaped such that the injection device 1 fits snugly within the injection device receiving channel 307 and there are multiple points or areas of contact between the exterior surface of the housing 10 of the injection device 1 and the lowermost surface of the supplementary device 2 when the supplementary device and the injection pen 1 are in this relative position. When the supplementary device 2 is located with respect to the injection pen 1 such that the protuberances 322 are located within the indents 107 respectively, the rib 105 is engaged within the rib receiving recess 318. Correct alignment of the supplementary device 2 with respect to the injection device 1 is thus provided in two ways: firstly, by the location of the rib 118 within the rib receiving recess 318 and secondly by the locating of the protuberances 322 within the indents 107.

It will be appreciated that the above arrangement prevents movement of the injection device 1 relative to the supplementary device 2. Movement of the supplementary device 2 in a radial direction from the injection device 1 is prevented by the collar 301 extending around the injection device 1. Movement of the supplementary device 2 in a radial direction from the injection device 1 is also prevented by the protuberances 322 engaging in the indents 107. The engagement of the protuberances 322 in the indents 107 also prevents movement of the supplementary device 2 along the longitudinal axis of the injection device 1 and about the longitudinal axis of the injection device 1. Additionally, movement of the supplementary device 2 about the longitudinal axis of the injection device and along the longitudinal axis of the injection device 1 is further prevented by the rib 105 being received in the rib receiving recess 318.

In order to remove the supplementary device 2 from the injection device 1, a user exerts a pressing force on the buttons 330 disposed on the outside of the body 300. The pressing force may be exerted by a finger and thumb. As the two buttons are depressed by the pressing force exerted by the user, the actuating element 332 on the rear side of each button 330 acts against the concave surface of the upper part 323 of each arm 320. Therefore, the upper part 323 of each arm 320 is biased to deform by the corresponding actuating element 332.

The support element 324 acts as a fulcrum and the arm 320 is urged to pivot about the support element. The distal end of the upper part 323 is prevented from moving by the tab 328 against which the upper part 323 is located. However, the free end 321 of the lower part 324 is free to move outwardly and so the lower part 324 pivots about the support element 324. Therefore, the protuberances 322 on each arm 320 are urged apart. This causes the protuberances 322 to disengage from the indents 107.

Once the protuberances 322 have been urged from the indents 107, the user may then rotate the rear end of the supplementary device 2 away from the injection device 1 about an axis extending perpendicular to the major axis of the opening 309. As the protuberances 322 are free of the indents 107, the user experiences relatively little resistance as the rear end of the body 300 is moved away from the injection device.

It will be understood that the cooperation between the rib 105 and the rib receiving recess 118 does not present any obstacle to separating the supplementary device 2 and the injection pen 1 in this way. The injection device 1 may then be slid from the aperture 306 formed in the collar 301.

Although in the above embodiment, the lower locating surface is defined by the lower part of the inner surface of the collar, it will be understood that the lower locating surface may be formed by another element on the lower part of the collar. Furthermore, a break may be formed in the collar.

Although in the above described embodiment the upper locating surface is defined by the upper part of the inner surface of the collar, it will be understood that the upper locating portion may be defined by the base of the channel. In such an arrangement, the inner surface of the collar and the base of the channel may be stepped from each other. The upper locating portion may be formed by another element on the upper part of the collar. Alternatively, the upper locating portion may be formed by another element on the base of channel.

The arms acting as support members are configured such that they are significantly resistant to movement in a direction along the longitudinal axis of the elongate body 300. Therefore, the elongate body 300 is prevented from moving in a direction along the longitudinal axis of the injection device 1 when the supplementary device is in engagement with the injection device 1. However, the support members on which the protuberances are disposed may have an alternative arrangement. In such an arrangement, the support members may have a flap arrangement or have a triangular structure with the protuberance at one corner and fixings to the elongate body of the supplementary device 2 at the other two corners. These two other corners may be separated in the axial length of the supplementary device 2. The triangular structure may comprise three limbs or it may be sheet-like. It may be planar or it may be curved. Although in the above described embodiments the support members are resilient, it will be understood that the support members may be rigid and the protuberances may be resilient. Alternatively both the support members and the protuberances may be resilient.

Referring now to FIGS. 13 to 20, an alternative form of the supplementary device 2 will now be described. Reference numerals are retained from above-described embodiments. The arrangement and configuration of many of the components and features are generally the same as described above, and so a detailed description will be omitted.

The supplementary device 2 has a body 400 and a collar 401. The body 400 is elongate and has a longitudinal axis. An upper part 408 of the collar 401 is integrally formed with the body 400. A lower part 409 of the collar extends from the upper part 408 of the collar 401. An injection device receiving channel 407 is formed in the lower side 403 of the body 400. The channel 407 is shown in dashed lines in FIG. 16. The channel 407 extends parallel to the longitudinal axis of the body 400. The channel 407 is arcuate in cross-section and is arranged to receive part of the rear section 102 of the injection device 1 therein.

The collar 401 comprises the upper part 408 which is defined at a front end 404 of the body 400 and the lower part 409, forming part of a closure 410. The upper part 408 and the lower part 409 together form an aperture 406 through which the injection device 1 is receivable. When the injection device 1 is received through the aperture 406, the rear section 102 of the injection device 1 is received between the body 400 and the closure 410. The closure 410 is hingedly mounted to the upper part 408, and therefore the body 400, by a hinge (not shown). The closure 410 is pivotably mounted to the body 400 about a rotational axis. Therefore, the lower part 409 of the collar 401 is pivotably mounted to the upper part 408. The closure 410 is configured to be pivoted towards the injection device 1 when the injection device 1 is received through the aperture 406 to secure the supplementary device 2 in a specific position relative to an outside surface of the injection device 1. The rotational axis of the closure 410 extends perpendicular to the longitudinal axis of the channel 407.

Figure 18:
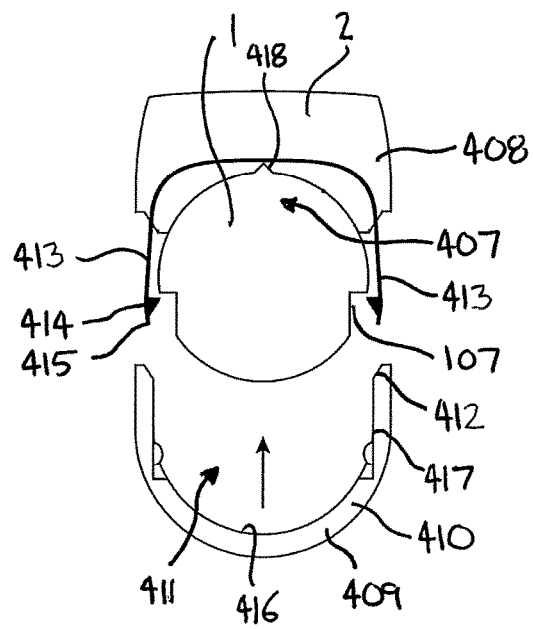
FIG. 18: a schematic cross-sectional rear view of the supplementary device shown in FIG. 13 releasably attached to the injection device of FIG. 1 with the closure in an unsecured position.

The closure 410 has a closure channel 411 formed therein (refer to FIG. 18). The closure channel 411 extends perpendicular to the rotational axis of the closure 410. The closure channel 411 is has an arcuate shape in cross-section and is arranged to receive part of the rear section 102 of the injection device 1 therein. Upper edges 412 of the closure 409 are chamfered. The upper edges 412 act as guide surfaces, as will become apparent hereinafter.

Figure 19:
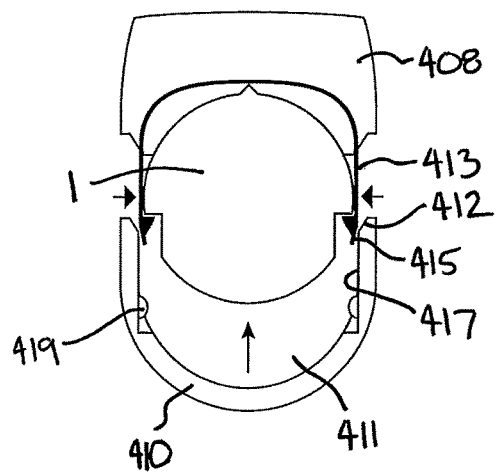
FIG. 19: a schematic cross-sectional rear view of the supplementary device shown in FIG. 13 releasably attached to the injection device of FIG. 1 with the closure in a partially secured position.
Figure 20:
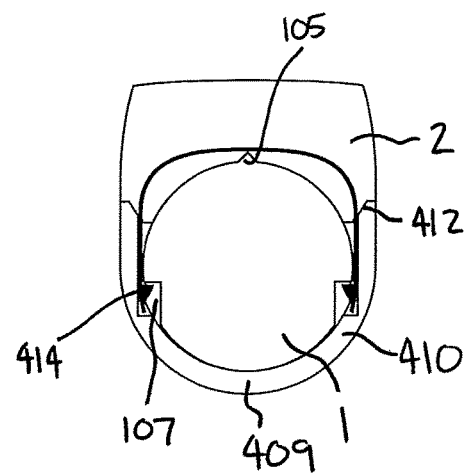
FIG. 20: a schematic cross-sectional rear view of the supplementary device shown in FIG. 13 releasably attached to the injection device of FIG. 1 with the closure in a secured position.

Left and right arms 413, acting as support members, extend from the lower side 403 of the body 400. The left arm 413 extends from the left side of the body 400, and the right arm extends from the right side of the body 400. As shown in FIGS. 18 to 20, the arms 413 depend substantially vertically from the lower side 403 of the body 400 of the supplementary device 2. Therefore, the arms 413 are formed on each side of the injection device receiving channel 407 and are spaced from each other.

A protuberance 414 is disposed at a free end 415 of each arm. The protuberances 414 act as engaging elements to engage in the indents 107 formed in the outer surface of the rear section 102 of the injection device 1. Each protuberance 414 is configured to be received in a corresponding indent 107. The protuberances 414 are shaped to correspond closely to the shapes of the indents 107 respectively. In this way, the protuberances 414 fit snugly within the corresponding indents 107 respectively when the supplementary device 2 is correctly positioned on the injection device 1. The external dimensions of the protuberances 414 are slightly smaller than the internal dimensions of the indents 107 so as to ensure that the protuberances 414 fit within their respective indent. The free end 415 of each arm 413 has a slight inward facing deflection so that the free ends 415 distend towards each other.

The arms 413 are splayed slightly away from each other extending from the body 400. Therefore, the ease of inserting the injection device there between is enhanced. Alternatively, the arms 413 extend parallel to each other. The arms 413 are resilient. Alternatively, a biasing element (not shown) such as a U-shaped spring may be coupled to each arm 413. The effect of the resilience of the arms 413 is to bias the arms into a certain position. The position into which the arms 413 are initially located is such that the distance between the innermost surfaces of the protuberances 413 is slightly greater than the diameter of the rear section 102 of the injection device 1. Therefore, the protuberances 414 are not initially urged into the indents 107 when they are aligned therewith.

The closure channel 411 formed in the closure 410 has an arcuate base 416 and two side faces 417 upstanding from the base 416. The arcuate base 416 of the closure channel 411 is configured to receive the rear section 102 of the injection device 1 so that the outer surface of the injection device 1 locates there against. The two side faces 417 extend parallel, but spaced from, each other. The width of the closure channel 411 between the opposing side faces 417 is slightly greater than the diameter of the rear section 102 of the injection device 1 so that the injection device 102 is receivable there between. The distance between the outer surface of each arm 413, on an opposing side to the protuberance formed thereon, is slightly greater than the width of the closure channel 411 between the opposing side faces 417. The side faces 417 act as guide elements to distend the arms 413 inwardly and retain the arms in an engaged position as will become apparent hereinafter.

Figure 14:
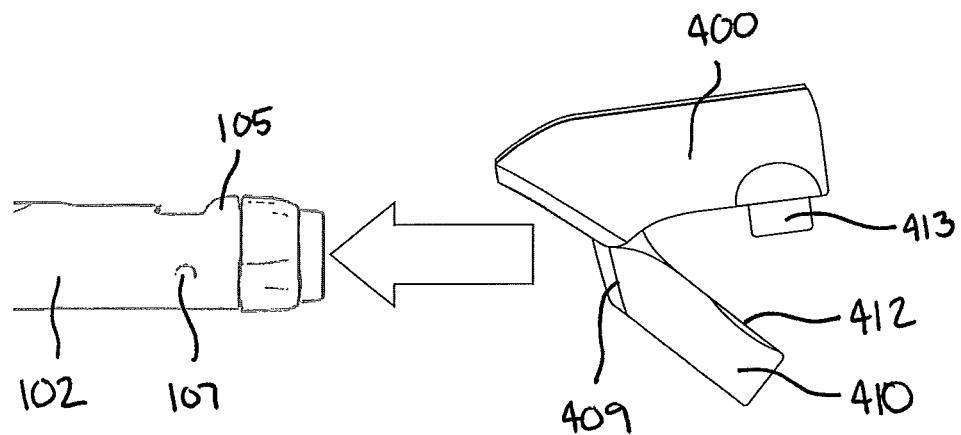
FIG. 14: a side view of the supplementary device shown in FIG. 13 orientated to be mounted to the injection device of FIG. 1.

As is shown in FIG. 14, the supplementary device 2 is initially located with respect to the injection pen 1 such that the aperture 406 of the collar 401 is aligned with the rear end of the injection device 1. The body 400 is orientated so that the longitudinal axis of the injection device receiving channel 407 is inclined with respect to the longitudinal axis of the injection device 1. The closure 409 is initially in an open position in which the closure 409 is rotated away from the body 400. Therefore the lower part 409 of the collar is rotated relative to the upper part 408.

Figure 15:
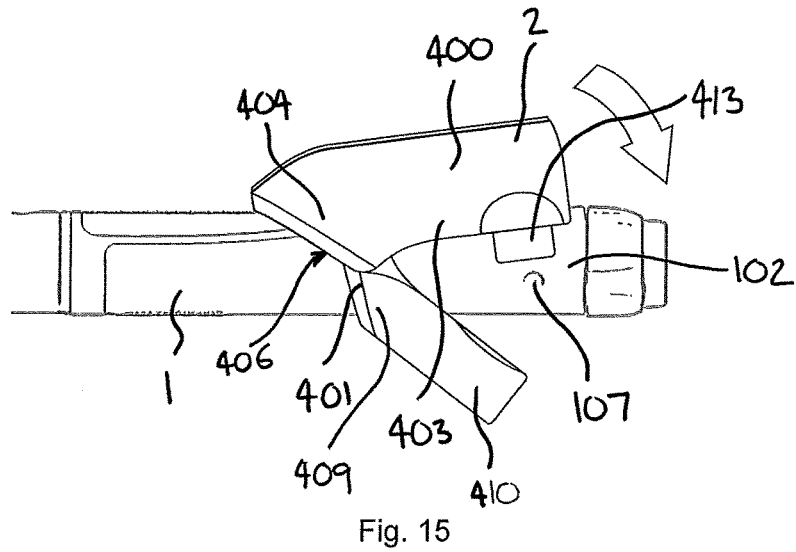
FIG. 15: a side view of the supplementary device shown in FIG. 13 with the injection device of FIG. 1 received through a collar of the supplementary device, prior to an engaging unit engaging with the indents on the injection device.

The collar 401 is then slid over the rear section 102 of the injection device 1, as shown in FIG. 15. Therefore, the rear section 102 of the injection device 1 is received through the aperture 406 of the collar 401. The supplementary device 2 is located with respect to the injection device 1 such that the ends of the right and left arms 413, in particular the protuberances 414, are just touching or are slightly spaced from the housing 10 of the injection device 1.

In order to locate the supplementary device 2 on the injection device 1, the body 400 of the supplementary device 2 is drawn towards the injection device 1 so that the rear section 102 of the injection device 1 is received in the injection device receiving channel 407. The injection device receiving channel 407 is shaped such that the injection device 1 is readily received in and locates against the injection device receiving channel 407. The arms 413 are disposed and extend either side of the injection device 1. However, the arms 413 are initially located such that the distance between the innermost surfaces of the protuberances 413 is slightly greater than the diameter of the rear section 102 of the injection device 1. Therefore, the protuberances 414 are not initially urged into the indents 107 when they are aligned therewith.

As the injection device 1 is located in the channel 407, the fin 105 protruding from the rear end of the injection device 1 is received in a fin receiving recess 418 (refer to FIGS. 18 to 20) formed in the channel 407. The user aligns the fin 105 with the recess 418 to ensure that the fin 105 is received in the recess 418 and the injection device and supplementary device 2 are aligned in the correct position with respect to each other.

In the event that the user places the supplementary device 2 onto the injection device 1 at a location such that the supplementary device 2 is rotated slightly about its longitudinal axis relative to its desired position, the rib 105 will not be received in the rib receiving recess 418 in the body 400. In this case, the supplementary device 2 is prevented from being located fully over the injection pen 1 by the rib 105 resting against the channel 407, spaced from the correct location within the rib receiving recess 418. Furthermore, the protuberances 414 will not be aligned with the corresponding indents 107. A user would know that the supplementary device 2 was not aligned correctly by the rear end of the supplementary device upstanding from the injection device 1. To correctly locate the supplementary device 2 in position with respect to the injection device 1, a user can simply rotate the supplementary device 2 relative to the injection device 1 about the longitudinal axis of the injection device 1. As the supplementary device 2 and the injection device 1 move relative to one another, the rib 105 and the rib receiving recess 418 become aligned with each other and the rib is received therein. At this point the protuberances 414 also align with the indents 107 and engage therewith.

Similarly, if the supplementary device 2 is not correctly aligned with the injection device 1 in a longitudinal direction, the rib 105 and rib receiving recess 418 will not be aligned and the rib will not locate in the recess. Relative movement of the supplementary device 2 and the injection device 1 in a direction along the longitudinal axis of the injection device 1 will cause the rib to locate in the recess and the protuberances to locate in the indents 107.

When the user has located the supplementary device 2 onto the injection device 1, in particular mating the locating rib 105 within the locating channel 418, the user may secure the supplementary device 2 to the injection device 1. This is achieved by the user moving the closure 410 from an open position, in which the closure 410 is rotated away from the body 400, and rotating the closure 410 towards the body 400 into a secured position. Movement continues until contact is made between the upper edge of the closure against a lower edge of the body.

Figure 16:
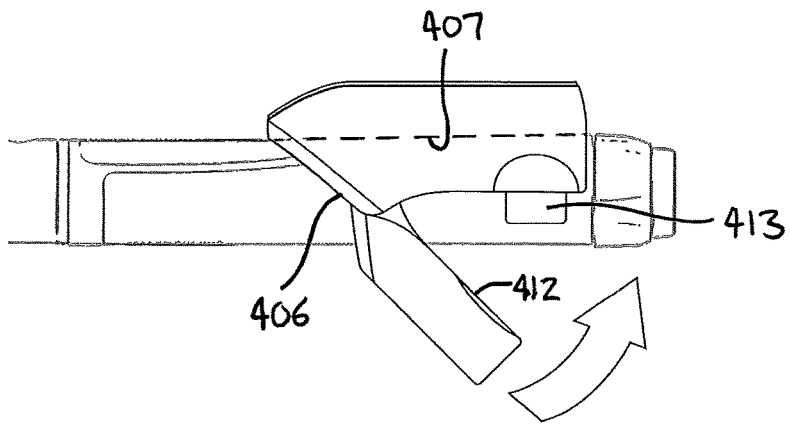
FIG. 16: a side view of the supplementary device shown in FIG. 13 with the injection device of FIG. 1 received through a collar of the supplementary device and the engaging unit engaged with the indents on the injection device.
Figure 17:
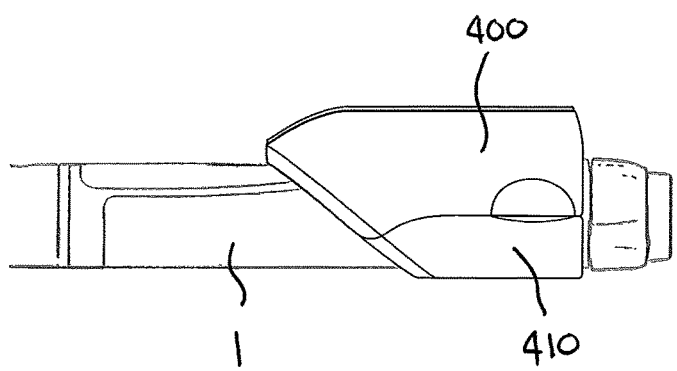
FIG. 17: a side view of the supplementary device shown in FIG. 13 with the injection device of FIG. 1 received through a collar of the supplementary device and a closure clamping the injection device.

In order to engage the protuberances 414 in the indents 107 and so mate the supplementary device 2 with the injection device 1, the user applies a force on the closure 107 to move the closure from an open position shown in FIGS. 16 and 18, and a secured position shown in FIGS. 17 and 20.

As the closure 410 is rotated relative to the body 400 to move from its open position to its secured position, the upper edges 412 of each side wall 417 of the closure channel 411 are brought into contact with the free ends 415 of the arms 413. As movement of the closure 410 towards the body 400 continues, the upper edges 412 of the side walls and the side walls 417 themselves act on the arms 413 and biases the free ends 415 of the arms 413 to distend inwardly towards the injection device 1 received in the injection device receiving chamber 407. As the injection device 1 is aligned in the injection device receiving chamber 407 in the correct position as described above, the protuberances 414 are aligned with the indents 107. Therefore, when the arms are biased inwardly towards each other, the protuberances 414 engage in the indents 107 formed in the outer surface of the injection device 1.

As best seen in FIG. 20, when the closure 410 is brought into its secured position and is engaged with the body 400, the injection device 1 is received in the closure channel 411 formed in the closure 410 and is clamped by the arms 413, as well as by the body 400 and the closure 410. The outer surface of the injection device 1 locates against the base 416 of the closure channel 411. The arms 413 are prevented from moving outwardly by the arms 413 locating against the side walls 417 of the closure channel 411. The closure 410 also ensures that the injection device 1 is tightly contained within the injection device receiving channel 407 and is held in place by the closure 410.

Movement of the supplementary device 2 along the longitudinal axis of the injection pen 1 is inhibited by the mating between the protuberances 414 and the indents 107. Additionally, rotation of the supplementary device 2 about the longitudinal axis of the injection device 1 is also inhibited by the mating between the protuberances 414 and the indents 107. Movement and rotation of the supplementary device 2 relative to the injection device 1 is further prevented by the locating rib 105 acting against the body 400 of the supplementary device 2.

Once the closure 410 is moved into its secured position, the injection device 1 is fully located within the injection device receiving channel 407. Here, the outermost surface of the display window 13 is aligned with the OCR. Correct alignment of the supplementary device 2 with respect to the injection device 1 is thus provided in two ways: firstly, by the location of the rib 105 within the rib receiving recess 418 and secondly by the locating of the protuberances 414 within the indents 107.

The closure 410 is retained in a secured position by a latch arrangement 419 formed on the closure 410 which engages with a catch arrangement formed on the body 400. One of the latch or the catch arrangements is biased towards the opposing arrangement so that when the latch and catch overlap the latch engages with the catch to retain the closure 410 in its secured position. The catch and/or latch arrangement is resilient, such that when a force is applied to the closure 410 to draw it away from the body 400, the engagement between the two arrangements is overcome and the closure 410 is then free to rotate relative to the body 400. In the present embodiment, the catch arrangement (not shown) is formed by the two arms, acting as support members, distending from the body 400. In this arrangement the catch is formed by the outer surface of each arm 413, although the catch may be an opening or recess formed in each arm 413, or be separate and spaced from the arm. The latch arrangement 419 is a protrusion formed on the side walls 417 of the closure channel 411. When the closure 410 is guided into its secured position, with the arms 413 being received in the closure channel 411 and locating against the side walls 417 of the closure channel 411, the arms 413 are urged towards the side walls 417 due to their resilience. Therefore, the protrusions on the side walls locate against the outer surface of each arm 413 and are urged thereagainst. Alternatively, the protrusions align with the opening or recess formed in the each arm, the arms are urged outwardly and the protrusions engage in the opening or recess. The closure 410 is then maintained in a secured position against the body 400 by the arms engaging the protrusions on the closure 410.

When a force is applied to the closure 410 to draw it away from the body 400, the engagement between the protrusions engaged in the opening or recess is overcome and the closure 410 is then free to rotate relative to the body 400. The retaining unit to retain the closure 410 in a secured position may be formed on one side of the closure 410 only.

As the closure 410 is drawn away from the body 400, the arms 413 slide along the side walls 417 of the closure channel 411 until the free end 415 of each arm 413 is drawn from the closure channel 411. Each arm is urged to distend outwardly into its initial position because the arms are resilient. Therefore, each arm 413 moves away from the injection device 1. When the arms 413 move away from each other, the protuberances 414 disengage from the indents 107 in the injection device 1.

Once the protuberances 414 have been urged from the indents 107, the user may then slide the injection device 1 from the aperture 406 formed in the collar 401 to separate the supplementary device 2 from the injection device 1.

Although the rib 105 and rib receiving recess aid orientation and alignment of the supplementary device 2 on the injection device 1 in the above described embodiments, it will be appreciated that in an alternative arrangement the rib 105 and rib receiving recess 318 are omitted and the correct alignment between the supplementary device 2 and the injection device 1 is provided by mating of the protuberances and the indents 107.

Other alternative arrangements for ensuring a correct relative position between the supplementary device 2 and the injection device 1 will be envisaged by the skilled person, and all such alternatives are within the scope of the invention except when explicitly excluded by the language of the claims.

When using embodiments of the present invention, the user inter alia has the following advantages:

The user can use the most convenient disposable insulin injector.

The supplementary device is attachable and detachable (reusable).

The alignment unit ensures that the optical sensor is aligned with the dosage display. Therefore, a user does not have to manually orientate the supplementary device.

The engaging unit ensures that the supplementary device is securely mounted to the injection device 1. Therefore, the supplementary device does not inadvertently detach from the injection device.

The release arrangement allows the engaging unit to be easily disengaged from the injection device. This allows the supplementary device to be drawn away from the injection device without undue effort from a user. Furthermore, damage to the supplementary device and injection device is prevented during engagement and disengagement of the supplementary device to the injection device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A supplementary device for attachment to a manually operable injection device, the supplementary device comprising
   a body having an injection device receiving channel; and
   a mating unit configured to releasably mount the body to the injection device in a specific position relative to an outside surface of the injection device,
   wherein the mating unit comprises a collar extending from the body,
   wherein the collar is configured to receive the injection device so that the injection device extends through the collar, and
   wherein the collar comprises a closure which is rotatable towards the body about an axis of rotation that is transverse to a longitudinal axis of the injection device receiving channel to secure the body to the injection device.

2. A supplementary device according to claim 1, wherein the mating unit further comprises an engaging unit configured to engage the supplementary device with the injection device.

3. A supplementary device according to claim 2, wherein the engaging unit comprises a support member having an engaging element, the engaging element being configured to engage in an indent on the injection device when the body is disposed in a specific position relative to an outside surface of the injection device.

4. A supplementary device according to claim 3, wherein the support member is a first support member and the engaging unit further comprises a second support member, engaging elements being disposed at the free end of each support member, and the free ends of the support members being biased towards each other.

5. A supplementary device according to claim 4, wherein each support member is pivotally mounted in the body about a mid-section so that the free ends of the support members may be biased away from each other to disengage the engaging elements from the indents.

6. A supplementary device according to claim 1, wherein the closure is configured to act on the support member to urge the engaging element into the indent when the closure is in its secured position so that the body is secured to the injection device.

7. A supplementary device according to claim 6, wherein the mating unit further comprises a catch arrangement configured to releasably retain the closure in its secured position.

8. A supplementary device according to claim 1, wherein the mating unit further comprises a locating recess in the body, the locating recess being configured to mate with a locating rib on the injection device.

9. A supplementary device according to claim 1, further comprising an optical reading arrangement and wherein the optical reading arrangement is directed at a display of the injection device when the body is mounted to the injection device in a specific position relative to an outside surface of the injection device.

10. A supplementary device according to claim 1, together with an injection device.

11. A supplementary device as claimed in claim 3, wherein the support member is disposed behind a wing which is formed from a transparent material.

12. A supplementary device for attachment to a manually operable injection device, the supplementary device comprising:
   a body having a front end and a rear end; and
   a mating unit configured to releasably mount the body to the injection device in a specific position relative to an outside surface of the injection device, wherein the mating unit comprises:
      a collar extending from the front end of the body at an acute angle to the longitudinal axis of the body and configured to receive the injection device so that the injection device extends through the collar;
      an engaging unit configured to engage the supplementary device with the injection device; and
      first and second locating surfaces spaced from each other to receive the injection device therebetween, wherein the first locating surface and the second locating surface are offset,
   wherein the collar comprises an opening,
   wherein the collar is configured to be pivoted about an axis extending perpendicular to the major axis of the opening between a first position in which the injection device is slidably receivable through the collar and a secured position in which the first and second locating surfaces are located against opposite outer surfaces of the injection device and positioned such that no part of the first locating surface is directly opposite the second locating surface when in the secured position, and
   wherein the engaging unit is configured to become engaged with the injection device as the collar is pivoted into the secured position.

13. A supplementary device according to claim 12, wherein the second locating surface is disposed between the first locating surface and the engaging unit.

14. A supplementary device according to claim 12 wherein the engaging unit further comprises a support member having an engaging element, the engaging element being configured to engage in an indent on the injection device when the collar is in the secured position.

15. A supplementary device according to claim 14, wherein the support member is a first support member and the engaging unit further comprises a second support member, wherein the engaging elements are disposed at the free end of each support member, and wherein the free ends of the support members are biased towards each other.

16. A supplementary device according to claim 14, wherein each support member is pivotally mounted in the body about a mid-section so that the free ends of the support members may be biased away from each other to disengage the engaging elements from the indents.

17. A supplementary device according to claim 12, wherein the mating unit further comprises a locating recess in the body, the locating recess being configured to mate with a locating rib on the injection device.

18. A supplementary device according to claim 12, further comprising an optical reading arrangement and wherein the optical reading arrangement is directed at a display of the injection device when the body is mounted to the injection device in a specific position relative to an outside surface of the injection device.

19. A supplementary device according to claim 12, together with an injection device.

20. A supplementary device as claimed in claim 14, wherein the support member is disposed behind a wing which is formed from a transparent material.

* * * * *